US008177811B2

(12) United States Patent
Tornier

(10) Patent No.: US 8,177,811 B2
(45) Date of Patent: May 15, 2012

(54) JOINT PROSTHESIS FOR TOTAL LUMBAR ARTHROPLASTY BY POSTERIOR APPROACH

(75) Inventor: Alain Tornier, Saint-Ismier (FR)

(73) Assignee: Clariance, Dainville (FR)

( * ) Notice: Subject to any disclaimer, the term of this patent is extended or adjusted under 35 U.S.C. 154(b) by 257 days.

(21) Appl. No.: 12/506,436

(22) Filed: Jul. 21, 2009

(65) Prior Publication Data
US 2010/0023058 A1 Jan. 28, 2010

Related U.S. Application Data

(60) Provisional application No. 61/083,674, filed on Jul. 25, 2008.

(51) Int. Cl.
*A61B 17/70* (2006.01)
(52) U.S. Cl. ...................................... 606/246; 606/264
(58) Field of Classification Search .......... 606/246–279, 606/70, 71, 280–284
See application file for complete search history.

(56) References Cited

U.S. PATENT DOCUMENTS

| 5,437,669 | A | * | 8/1995 | Yuan et al. ..................... 606/278 |
| 5,470,333 | A | * | 11/1995 | Ray ............................... 606/261 |
| 5,885,290 | A | * | 3/1999 | Guerrero et al. ................ 606/71 |
| 6,187,005 | B1 | * | 2/2001 | Brace et al. .................... 606/264 |
| 7,294,129 | B2 | * | 11/2007 | Hawkins et al. ............. 606/86 A |
| 7,544,174 | B2 | * | 6/2009 | Nathanson ...................... 602/16 |
| 7,563,283 | B2 | * | 7/2009 | Kwak ........................ 623/17.11 |
| 7,604,652 | B2 | * | 10/2009 | Arnin et al. .................... 606/249 |
| 7,691,145 | B2 | * | 4/2010 | Reiley et al. ............... 623/17.11 |
| 7,799,054 | B2 | * | 9/2010 | Kwak et al. .................... 606/246 |
| 7,887,566 | B2 | * | 2/2011 | Hynes ............................ 606/254 |
| 2004/0002708 | A1 | * | 1/2004 | Ritland ........................... 606/61 |
| 2004/0111091 | A1 | * | 6/2004 | Ogilvie et al. .................. 606/73 |
| 2004/0254574 | A1 | * | 12/2004 | Morrison et al. ............... 606/61 |
| 2005/0055096 | A1 | * | 3/2005 | Serhan et al. ............... 623/17.11 |
| 2006/0084991 | A1 | * | 4/2006 | Borgstrom et al. ............. 606/61 |
| 2006/0149229 | A1 | * | 7/2006 | Kwak et al. ..................... 606/61 |
| 2006/0149230 | A1 | | 7/2006 | Kwak et al. |
| 2006/0200130 | A1 | * | 9/2006 | Hawkins et al. ................ 606/61 |
| 2006/0271046 | A1 | * | 11/2006 | Kwak et al. ..................... 606/61 |

(Continued)

FOREIGN PATENT DOCUMENTS

WO WO 2006/039260 A2 4/2006
WO WO 2006/073593 A2 7/2006

OTHER PUBLICATIONS

French Search Report dated Mar. 16, 2009.

*Primary Examiner* — Pedro Philogene
(74) *Attorney, Agent, or Firm* — Young & Thompson

(57) ABSTRACT

The total arthroplasty joint prosthesis includes connectors (2, 4) fixed in the pedicles Vp of the spinal levels by anchoring screws (3), upper and lower connecting elements (5, 6) connecting the connectors (2, 4) to each other, and guiding and damping element (7) connecting the upper and lower connecting elements (5, 6), the guiding and damping element (7) and the upper and lower connecting elements (5, 6) being constructed with relation to each other so as to define at least one rotation and sliding axis C situated at the level of the upper superjacent vertebra Va of the instrumented segment Sr in order to limit the stresses on the anchoring screws (3) ensuring fixation of the connectors (2) in the superjacent vertebra Va.

12 Claims, 7 Drawing Sheets

U.S. PATENT DOCUMENTS

| | | | |
|---|---|---|---|
| 2006/0282075 A1* | 12/2006 | Labrom et al. | 606/61 |
| 2007/0073289 A1* | 3/2007 | Kwak et al. | 606/61 |
| 2007/0173828 A1* | 7/2007 | Firkins et al. | 606/61 |
| 2007/0191831 A1* | 8/2007 | Sanders et al. | 606/61 |
| 2007/0293864 A1* | 12/2007 | Reimels et al. | 606/69 |
| 2008/0015585 A1* | 1/2008 | Berg et al. | 606/61 |
| 2008/0045950 A1* | 2/2008 | Dewey | 606/61 |
| 2008/0275555 A1* | 11/2008 | Makower et al. | 623/14.12 |
| 2009/0149885 A1* | 6/2009 | Durward et al. | 606/246 |
| 2010/0087867 A1* | 4/2010 | Klein et al. | 606/278 |

* cited by examiner

JOINT PROSTHESIS FOR TOTAL LUMBAR ARTHROPLASTY BY POSTERIOR APPROACH

CROSS-REFERENCE TO RELATED APPLICATIONS

The instant application claim benefit of priority to Application No. 61/083,674 filed Jul. 25, 2008.

STATEMENT REGARDING FEDERALLY SPONSORED RESEARCH OR DEVELOPMENT

None.

THE NAMES OF THE PARTIES TO A JOINT RESEARCH AGREEMENT

None.

INCORPORATION-BY-REFERENCE OF MATERIAL SUBMITTED ON A COMPACT DISC

None.

BACKGROUND OF THE INVENTION

1. Field of the Invention

The present invention relates to a total joint arthroplasty prosthesis allowing the elements for guiding the superjacent and subjacent lumbar vertebrae of a spinal segment to be reconstructed with a center of rotation and means for limiting movements ensuring the necessary stability of said vertebrae.

2. Description of Related Art

In certain cases of patients with degenerative lumbar spine pathologies, such as joint stenosis or arthrosis, completely fusing the superjacent and subjacent lumbar vertebrae of the spinal segment is expected.

In young patients where the deterioration of the lumbar vertebrae may be reversible, using dynamic stabilization devices henceforth, especially as a first intention, is expected.

In cases of elderly patients where the deterioration of the lumbar vertebrae are more severe and especially irreversible, decompressing the spinal marrow and the nerve roots is expected, necessitating the elimination of certain hypertrophied bone elements. This technique generally leads to destabilization of the spinal segment, requiring the superjacent and subjacent lumbar vertebrae to be fused to each other.

It has been observed that fusion of the superjacent and subjacent lumbar vertebrae to each other may, in certain cases, present complications leading to the degeneration of the adjacent spinal levels that are overstimulated due to said fusion.

BRIEF SUMMARY OF THE INVENTION

The object of the total joint arthroplasty prosthesis according to the present invention is, when destabilization of the spine has been created, to be able to stabilize the affected spinal segment Sr while protecting to term the other spinal levels from risks of deterioration.

The total joint arthroplasty prosthesis according to the present invention comprises connectors fixed in the pedicles Vp of the spinal levels by anchoring screws, upper and lower connecting elements connecting the connectors to each other, and guiding and damping means connecting said upper and lower connecting elements, said guiding and damping means and said upper and lower connecting elements being constructed with relation to each other so as to define at least one rotation and sliding axis C situated at the level of the upper superjacent vertebra Va of the instrumented segment Sr in order to limit the stresses on the anchoring screws ensuring fixation of the connectors in said superjacent vertebra Va.

The total joint arthroplasty prosthesis according to the present invention comprises limitation means that connect the connectors between each other and that enable the flexion extension and lateral inflexion movements around the rotation and sliding axis C to be limited.

The total joint arthroplasty prosthesis according to the present invention comprises limitation means that are comprised of a cable connecting the connectors between each other.

The total joint arthroplasty prosthesis according to the present invention comprises guiding and damping means that are comprised of a connecting support comprising an oblong groove inside of which is housed a guiding element cooperating with the connecting element and elastomer stops whose elastic deformations enable the displacements of said guiding element inside said oblong groove to be limited without constraint and guiding and fixation means cooperating with the lower connecting element.

The total joint arthroplasty prosthesis according to the present invention comprises a guiding element that is comprised of a first plate integral with a hollow sleeve on which a second plate is connected, said guiding element being connected to the first upper connecting element through a clamping screw traversing the hollow sleeve to cooperate with a nut, said hollow sleeve traversing the oblong groove of the connecting support such that its displacements are limited by the elastic deformation of the elastomer stops.

The total joint arthroplasty prosthesis according to the present invention comprises a connecting support that is connected to the second lower connecting element on the one hand by means of a guiding device and on the other hand by means of a blocking device.

The total joint arthroplasty prosthesis according to the present invention comprises a first upper connecting element that is comprised of a central body extending at each end by rods on which a slit bush with a spherical profile respectively slides intended to cooperate with each first connector, said central body being pierced by an oblong hole for cooperation with the guiding and damping means.

The total joint arthroplasty prosthesis according to the present invention comprises a second lower connecting element that is comprised of a central part laterally comprising extensions, each presenting a fork-shaped end provided to come around the corresponding anchoring screw, said central part comprising a guiding device and threaded bores for the positioning and immobilization of guiding and damping means.

The total joint arthroplasty prosthesis according to the present invention comprises first connectors that are each comprised of a body presenting a bore for the passage of the pedicle screw, a housing for the reception of the first upper connecting element, a threaded bore perpendicularly culminating in a hole and cooperating with a clamping screw for the immobilization of limitation means when the latter are introduced into the through hole and a slot traversing the hole and the bore to culminate inside the housing so as to allow said housing to be deformed under a pressure force generated by a clamping nut when the first connector is immobilized on the corresponding pedicle screw.

The total joint arthroplasty prosthesis according to the present invention comprises second connectors that are each comprised of, on the one hand, a connection element forming a rod comprising, along a horizontal direction, a fork presenting an oblong opening for its passage around the pedicle screw, and extending along a perpendicular direction by an anchoring rod equipped with an end in the shape of a strip and, on the other hand, a connecting ring pierced in its middle by a hole for its positioning around the same anchoring screw, said connecting ring is pierced with through holes allowing the positioning and immobilization of the limitation means.

The total joint arthroplasty prosthesis according to the present invention comprises a connecting ring comprising lower lateral edges cooperating with the fork such that said ring may not pivot in rotation with relation to the anchoring screw when the nut is tightened.

The total joint arthroplasty prosthesis according to the present invention comprises a connecting ring comprising upper lateral edges that are disposed according to a direction perpendicular to that of the lower lateral edges for guiding the second lower connecting element.

BRIEF DESCRIPTION OF THE SEVERAL VIEWS OF THE DRAWINGS

The attached drawings, given by way of example, allow the invention, the characteristics that the invention presents and the advantages that the invention is likely to bring to be better understood.

DETAILED DESCRIPTION OF THE INVENTION

Figure 1:
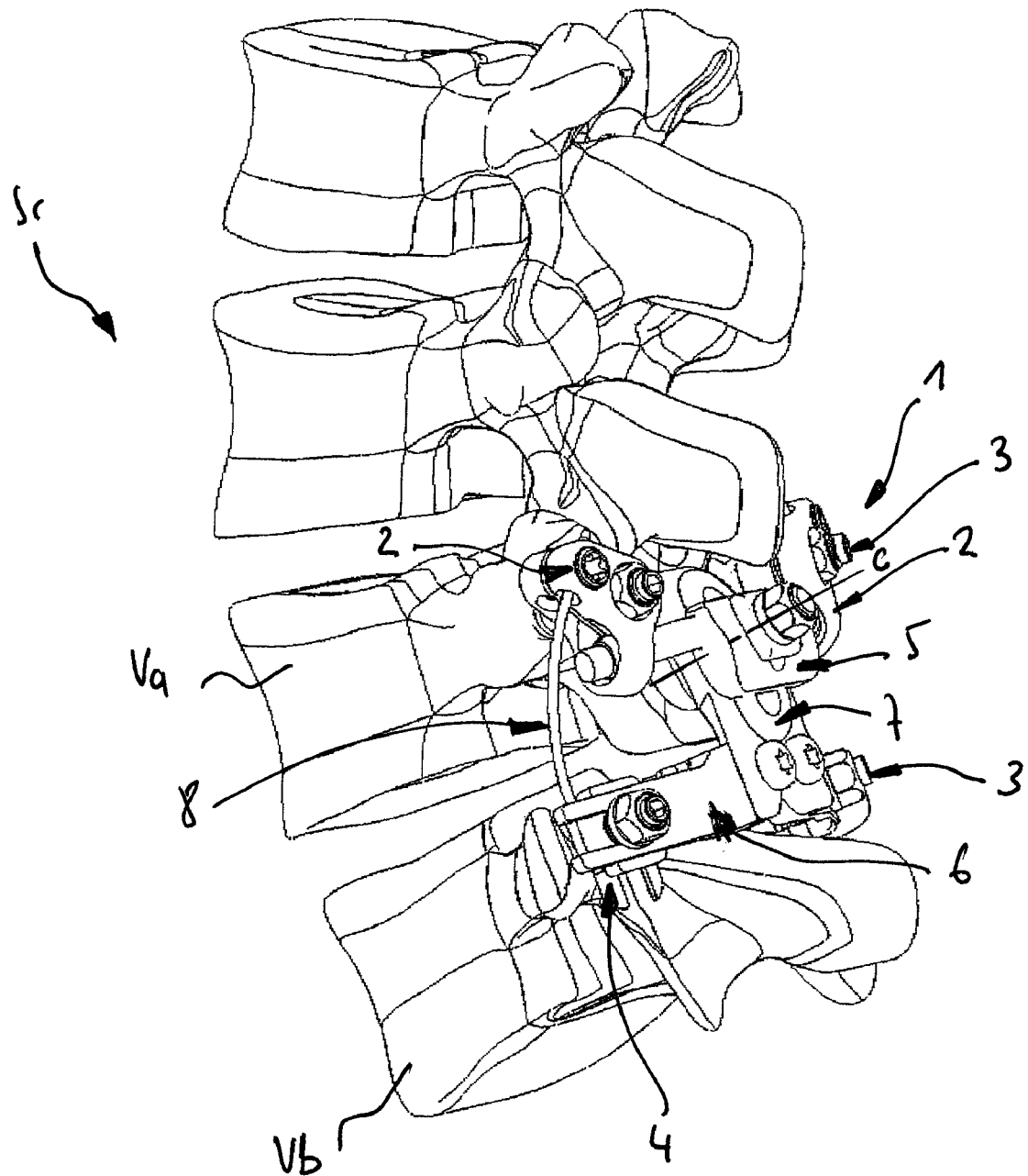
FIGS. 1 and 2 are views illustrating a spinal segment from a vertebral column on which the total joint arthroplasty prosthesis according to the present invention has been mounted on the spinal level.
Figure 2:
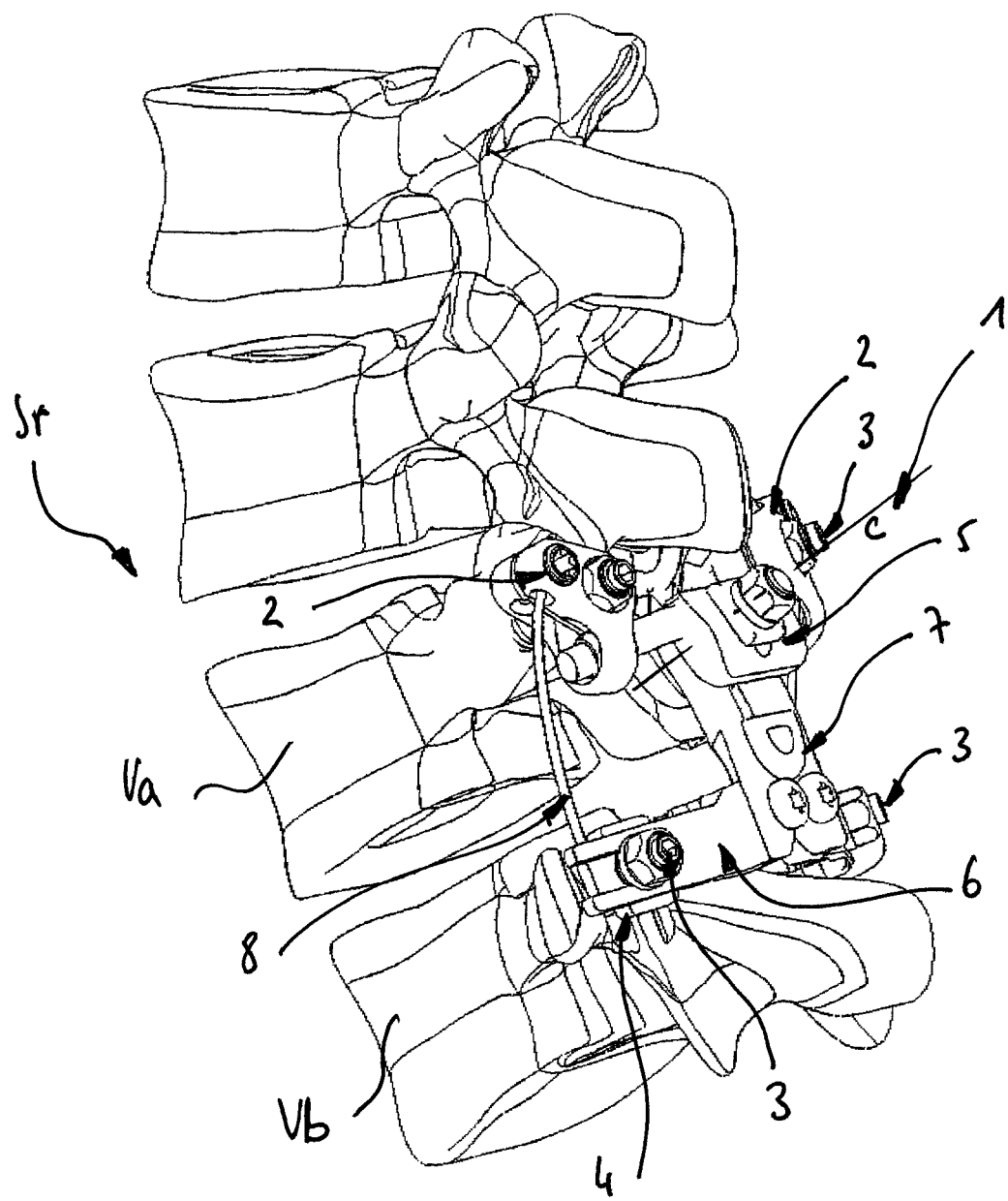
Figure 3:
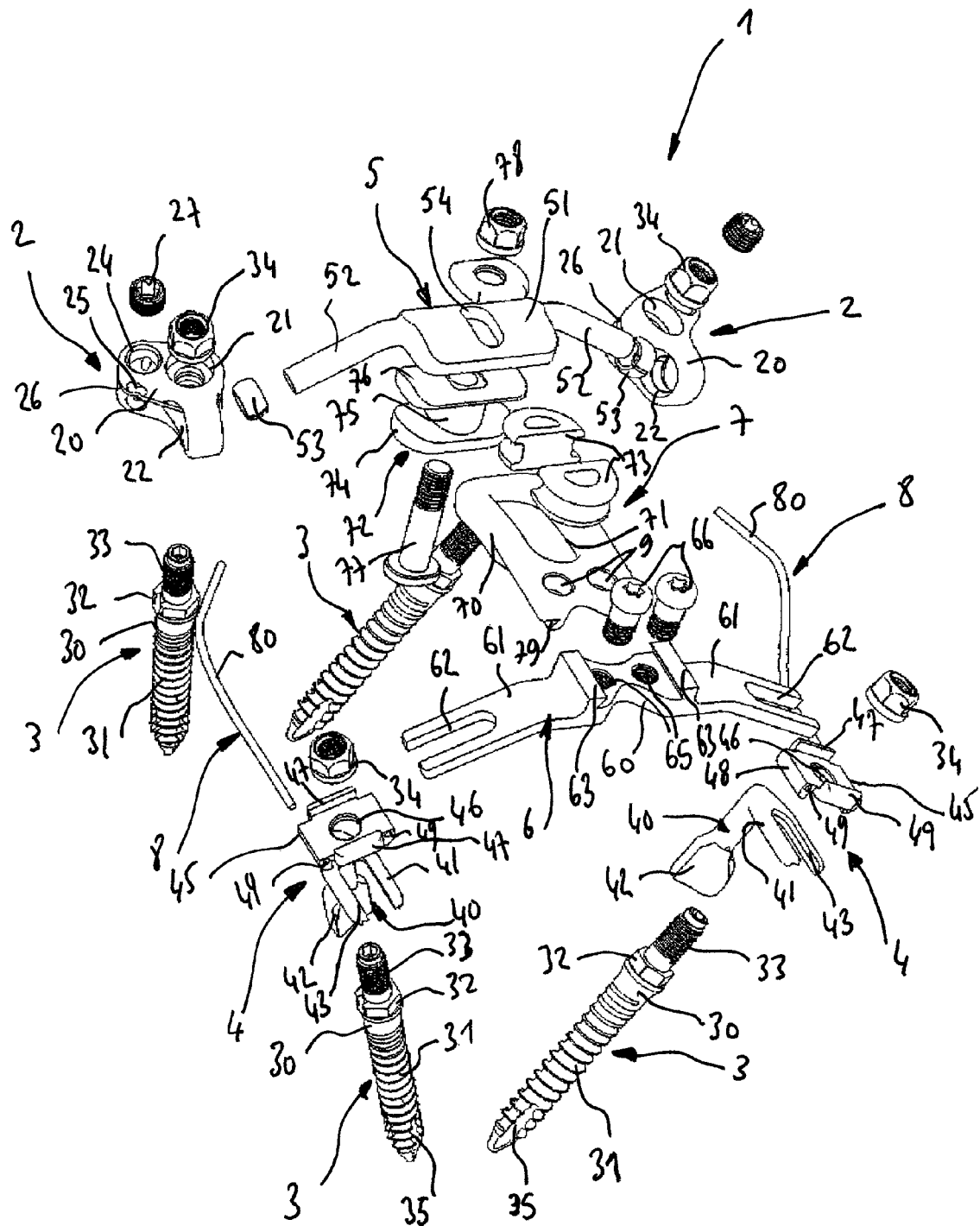
FIG. 3 is a blow-up perspective view representing the different elements constituting the total joint arthroplasty prosthesis according to the present invention.
Figure 4:
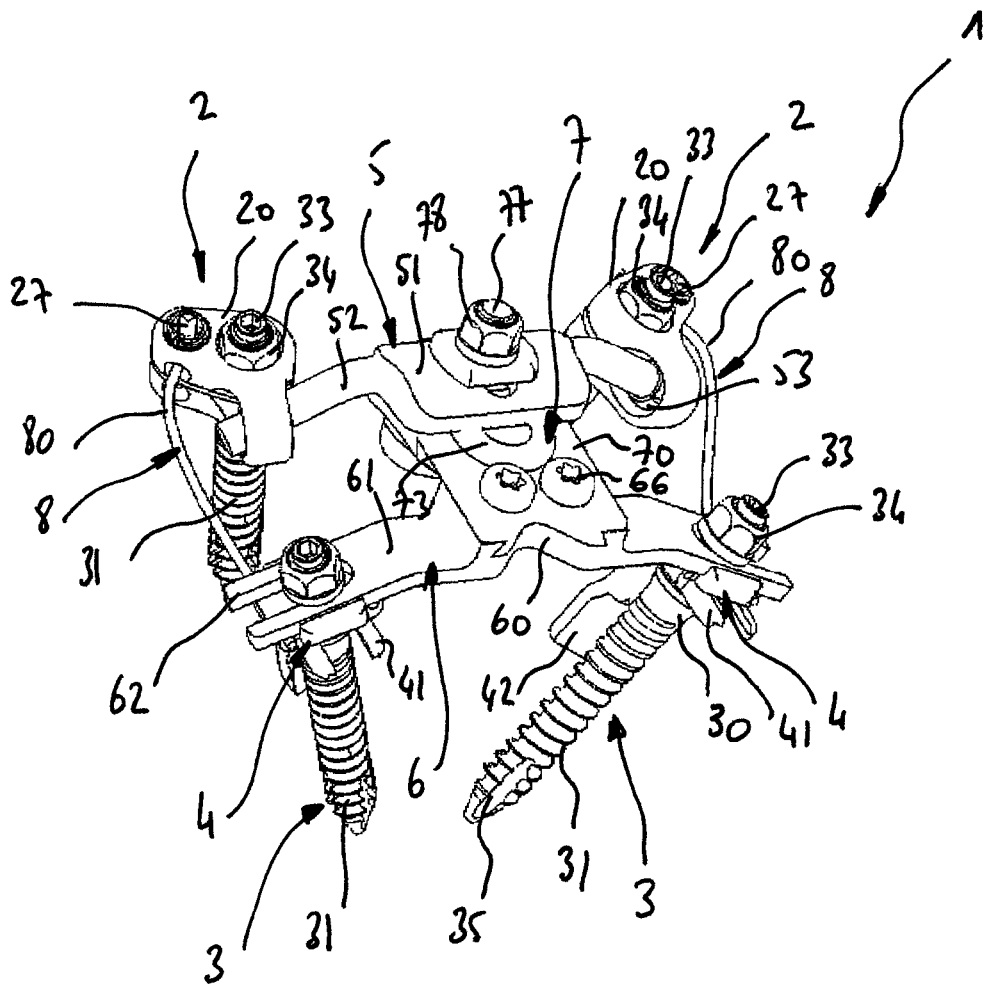
FIG. 4 is a perspective view showing the assembly of different elements constituting the total joint arthroplasty prosthesis according to the present invention.

FIGS. 1 to 4 show an instrumented spinal segment Sr of a vertebral column wherein certain vertebrae, more particularly the superjacent Va and subjacent Vb lumbar vertebrae, are connected to each other by a total joint arthroplasty prosthesis 1.

The joint prosthesis 1 comprises, on the one hand, first connectors 2 through an anchoring screw 3 fixed in the pedicles Vp of the superjacent lumbar vertebra Va and, on the other hand, second connectors 4 through other anchoring screws 3 fixed in the pedicles Vp of the subjacent lumbar vertebra Vb.

The joint prosthesis 1 comprises a first upper connecting element 5 allowing the first connectors 2 integral with the pedicles Vp of the superjacent lumbar vertebra Va to be connected to each other.

The joint prosthesis 1 comprises a second lower connecting element 6 allowing the second connectors 4 integral with the pedicles Vp of the subjacent lumbar vertebra Vb to be connected to each other.

The joint prosthesis 1 comprises guiding and damping means 7 connecting the first upper connecting element 5 with the second lower connecting element 6 and ensuring controlled flexion extension and lateral inflexion movements of the superjacent Va and subjacent Vb lumbar vertebrae.

The guiding and damping means 7 and the upper and lower connecting elements 5, 6 are constructed with relation to each other so as to define at least one rotation and sliding axis C situated at the level of the upper superjacent vertebra Va of the instrumented segment Sr in order to limit the stresses on the anchoring screw 3 ensuring fixation of connectors 2 in said superjacent vertebra Va.

The joint prosthesis 1 comprises limitation means 8 connecting the first connectors 2 with the corresponding second connectors 4 ensuring limitation of the flexion extension and lateral inflexion movements of the superjacent Va and subjacent Vb lumbar vertebrae. The limitation means 8 connecting the connectors 2, 4 between them allow the flexion extension and lateral inflexion movements around the rotation and sliding axis C of the joint prosthesis 1 to be limited.

The joint prosthesis 1 comprises double-threaded pedicle anchoring screws 3 that are known in themselves and constituted of a longitudinal body 30 presenting a threaded part 31 intended for the anchoring of said screw into the bone body of the pedicles Vp of each superjacent and subjacent lumbar vertebra Va, Vb of the spinal segment Sr to be instrumented.

The longitudinal body 30 comprises, in the extension of the threaded part 31, a clamping head 32 integral with a threaded cylindrical profile 33 allowing a clamping nut 34 to be positioned.

Also, the pedicle screws 3 may be cannulated with the lateral openings 35 allowing biological cement intended to improve the anchoring in each superjacent and subjacent lumbar vertebra Va, Vb of the spinal segment Sr to be instrumented to be injected.

The first connectors 2 are each constituted of a body 20 presenting a bore 21 for the passage of the threaded cylindrical profile 33 of the pedicle screw 3 along a perpendicular direction and, offset laterally to said bore, a housing 22 with a spherical profile cooperating with the first upper connecting element 5.

The first upper connecting element 5 is constituted of a central body 51 extending at each end by rods 52 on which respectively slide a slit bush with a spherical profile 53 intended to cooperate with the housing 22 of each connector 2 and allow the angular positioning of said upper connecting element 5 with relation to said connector. The central body 51 of the first upper connecting element 5 is pierced by an oblong hole 54 wherein the longitudinal axis is perpendicular to that of rods 52.

The body 20 of each first connector 2 is pierced vertically by a threaded bore 24 culminating perpendicularly in a hole 25 traversing said body. The threaded bore 24 cooperates with a clamping screw 27 allowing the limitation means 8 to be immobilized when the latter are introduced into the through hole 25.

The means for limiting 8 the flexion extension and lateral inflexion movements are constituted of a cable 80 formed for example by a central strand around which six other strands are twisted.

The body 20 of each first connector 2 presents a slot 26 traversing the hole 25 and the bore 21 to culminate inside the housing 22 so as to enable said housing to be deformed under a pressure force generated by the clamping nut 34 when said connector is immobilized on the corresponding pedicle screw 3.

The second connectors 4 are each comprised of a connection element forming a rod 40 comprising, along a horizontal direction, a fork 41 extending along a perpendicular direction by a backer rod 42.

The fork 41 presents an oblong opening 43 that cooperates with the threaded cylindrical profile 33 of each anchoring screw 3, while the backer rod 42 presents an end in the shape of a strip that is supported against the external bone part of the corresponding vertebra along a direction that is substantially parallel to that of the threaded part 31 of the anchoring screw 3 in order to reinforce the pedicle anchoring and resist being out of plumb.

The oblong opening 43 of the fork 41 presents a profile that is adapted around the clamping head 32 of the anchoring screw 3 so that the connection element 40 forming a rod cannot be driven in rotation when the nut 34 is tightened.

The second connectors 4 each comprise a connecting ring 45 pierced in its middle by a hole 46 for its placement around the threaded cylindrical profile 33 of the anchoring screw 3. The connecting ring 45 comprises a lower face supported on fork 41.

The lower face comprises lateral edges 47 cooperating with the external edges of each branch constituting the fork 41 such that the ring 45 cannot pivot in rotation with relation to the anchoring screw 3 when the nut 34 is tightened.

The lateral edges 47 of the lower face of each connecting ring 45 are respectively pierced by a through hole 49 allowing the cable 80 of the limitation means 8 to be positioned and immobilized.

The connecting ring 45 comprises an upper face equipped with lateral edges 48 that are disposed along a direction perpendicular to that of the lateral edges 47 of the lower face.

The upper face of the connecting ring 45 of each connection element 40 forming a rod is provided to cooperate with, before the nut 34 is tightened, the second lower connecting element 6.

The second lower connecting element 6 is constituted of a central part 60 laterally comprising extensions 61, each presenting an end in the form of a fork 62. The branches of the fork 62 of each extension 61 are provided to come around the threaded cylindrical profile 33 of the corresponding anchoring screw 3 while being laterally guided, before the nut 34 is tightened, by the lateral edges 48 of the upper face of the connecting ring 45.

The central part 60 of the second lower connecting element 6 laterally comprises, along a direction perpendicular to that of extensions 61, a guiding device 63 whose profile may be, for example, a dovetail.

The central part 60 is pierced between the lateral edges of the guiding device 63 by two threaded bores 65 respectively cooperating with a clamping screw 66 for immobilizing in translation a connection support 70 belonging to the guiding and damping means 7 allowing the first upper connection element 5 to be connected to the second lower connecting element 6.

The connection support 70 comprises in its middle an oblong groove 71 inside of which is housed a guiding element 72 and, on each side of the latter, elastomer stops 73 whose elastic deformations allow the displacements of said guiding element 72 inside said oblong groove 71 to be limited without constraint.

The guiding element 72 is constituted under the connection support 70 of a first plate 74 integral with a hollow sleeve 75 traversing the oblong groove 71 and on which a second plate 76 is fitted above said connecting support 70.

The guiding element 72 is connected to the central body 51 of the first upper connection element 5 through a clamping screw 77 traversing the hollow sleeve 75 and the oblong hole 54 to cooperate with a nut 78.

The connection support 70 is connected to the central part 60 of the second lower connecting element 6 by a guiding device 79 whose profile, complementary to that of the guiding device 63, allows said connection support 70 to slide in the central part 60 of the second lower connecting element 6.

The connection support 70 is pierced by two holes 9, each traversed by a clamping screw 66 cooperating with the threaded bores 65 for the fixation of said connection support 70 on the central part 60 of the second lower connecting element 6.

Figure 5:
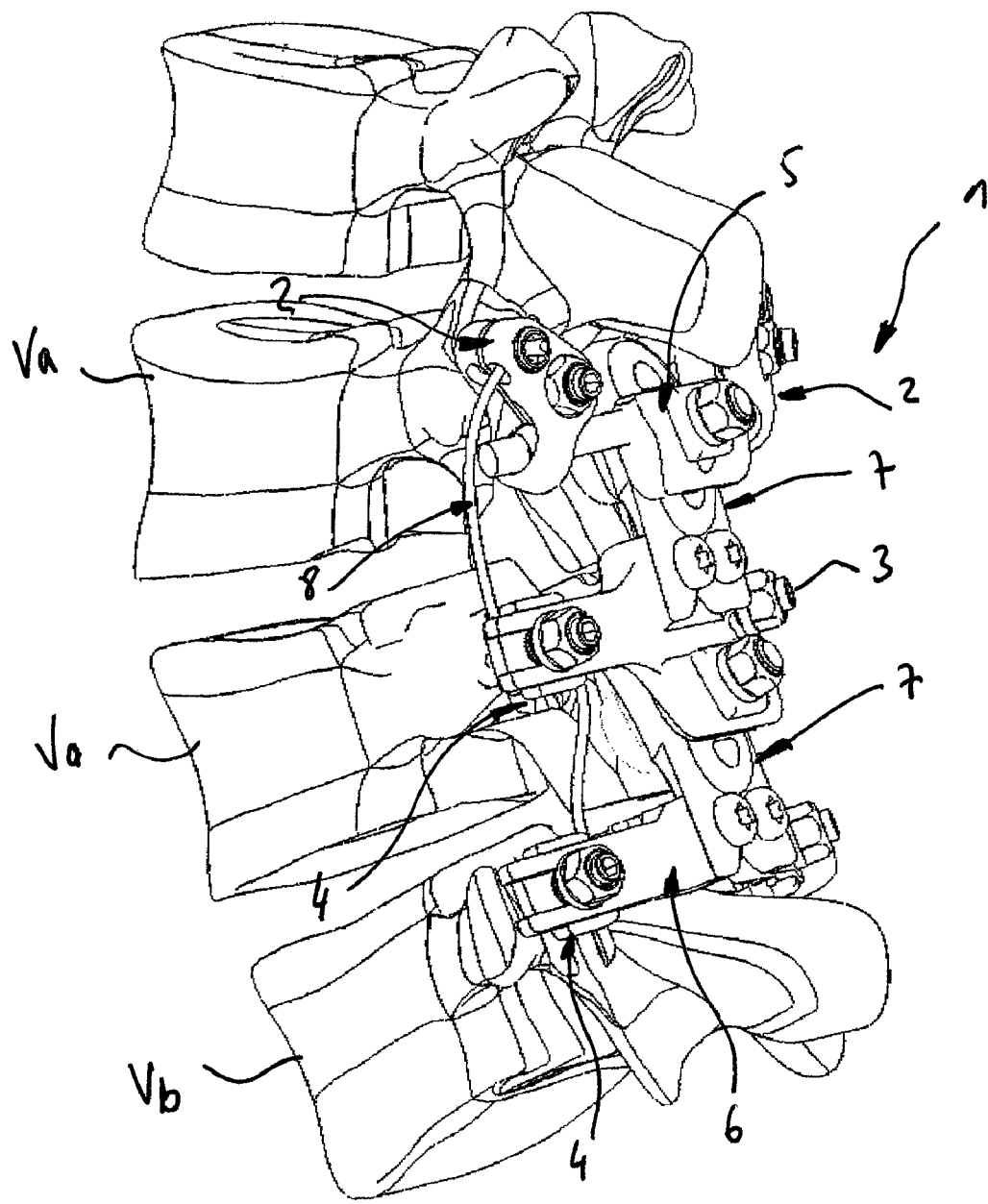
FIG. 5 is a view illustrating a spinal segment of a vertebral column on which the total joint arthroplasty prosthesis according to the present invention has been assembled on at least two spinal levels.
Figure 6:
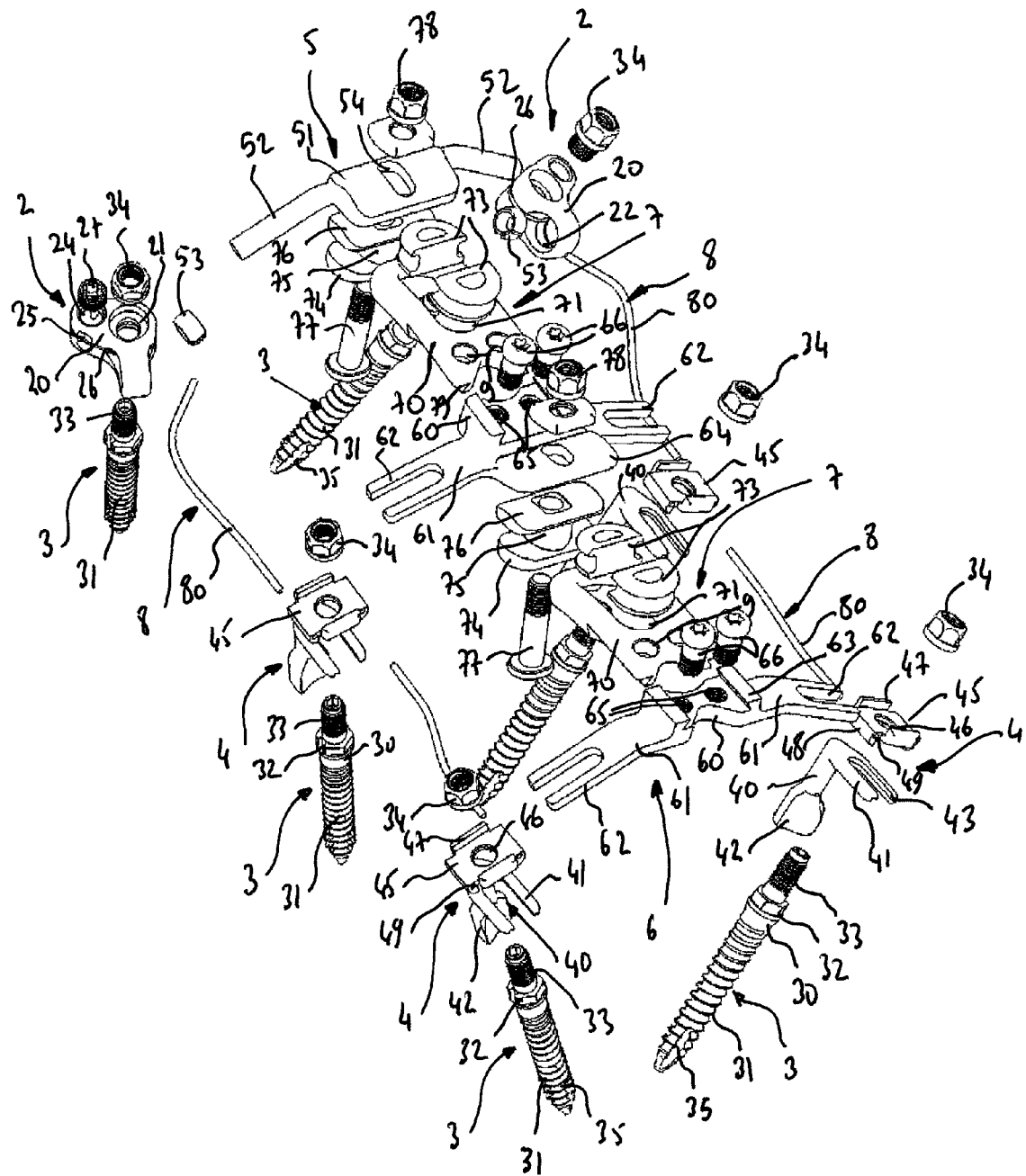
FIG. 6 is blow-up perspective view representing the different elements constituting the total joint arthroplasty prosthesis to connect at least two spinal levels according to the present invention.
Figure 7:
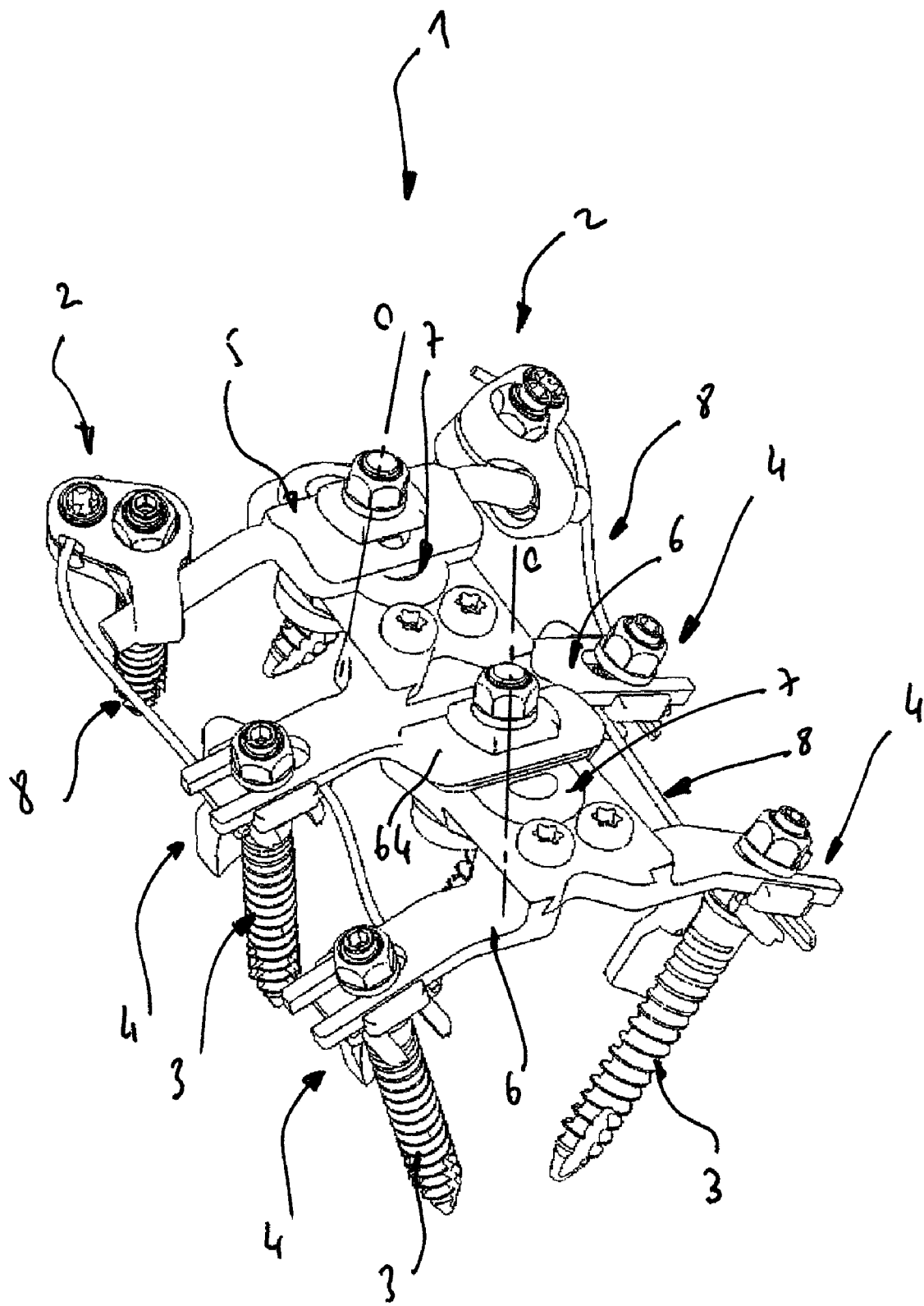
FIG. 7 is perspective view showing the assembly of the different elements constituting the total joint arthroplasty prosthesis to connect at least two spinal levels according to the present invention.

FIGS. 5 to 7 show the assembly and mounting of the total joint arthroplasty prosthesis 1, for example, on two spinal levels Va, Vb and Vc of a spinal segment Sr to correct. Vertebrae Va and Vb are extreme vertebrae of the spinal segment Sr to be instrumented, while vertebra Vc is found between said vertebrae Va and Vb.

In the same manner as the previous, first and second connectors 2, 4, each connected by upper and lower connecting elements 5, 6 of the total joint arthroplasty prosthesis 1, are respectively fixed on pedicles Vp of vertebrae Va, Vb through anchoring screws 3.

At the level of the pedicles Vp of the intermediate vertebra Vc are fixed, by means of anchoring screws 3, other connectors 4 that are identical to those fixed in the pedicles of vertebra Vb.

Connectors 4 of vertebra Vc are connected between each other by a median connecting element 6 similar in part to that connecting the connectors 4 of vertebra Vb. The median connecting element 6 of the vertebra Vc is mainly distinguished from that described previously in that the central part 60 comprises, between extensions 61, a lateral skirt 64 pierced in its middle by an oblong hole 67.

This lateral skirt 64 presents the same characteristics and advantages as the central body 51 of the first upper connection element 5 in order to allow the fixation of the guiding element 72 of the guiding and damping means 7 through a clamping screw 77 traversing the hollow sleeve 75 and the oblong hole 67 to cooperate with the nut 78.

This lateral skirt 64 of the median connecting element 6 enables another guiding and damping means 7 to be placed and held, means 7 are identical to those described previously except they are between spinal levels Vc, Vb.

Thus, the upper connection element 5 fixed on vertebra Va is connected to the median connecting element 6 of vertebra Vc by guiding and damping means 7 similar to those described previously, while the median connecting element 6 is connected to the lower connecting element 6 of vertebra Vb by other guiding and damping means 7.

Also, connectors 2 and 4 of spinal levels Va, Vc and connectors 4 of spinal levels Vc, Vb are respectively connected by first and second cables 80 constituting the means 8 for limiting the flexion extension and lateral inflexion movements.

Thus, the total joint arthroplasty prosthesis 1 integral with superjacent and subjacent vertebrae Va and Vb or vertebrae Va, Vc, Vb allows, when the spine has been destabilized, the spinal segment Sr to be able to be stabilized while protecting the other spinal levels from deterioration.

In fact, the total joint arthroplasty prosthesis 1 enables, by its structure and the various elements making it up, the guiding elements of the superjacent Va and subjacent Vb lumbar vertebrae of a spinal segment Sr of a vertebral column to be reconstructed.

In addition, it must be understood that the previous description was only given by way of example and that it in no way limits the field of the invention from which one will not depart by replacing the details of embodiment described by any other equivalents.

The invention claimed is:

1. A total joint arthroplasty prosthesis allowing the guiding elements of a superjacent Va and subjacent Vb lumbar vertebrae of a spinal segment Sr of a vertebral column to be reconstructed, the prosthesis comprising:
connectors (2, 4) adapted to be fixed in pedicles Vp of the spinal levels by anchoring screws (3), upper and lower connecting elements (5, 6) connecting the connectors (2, 4) between each other, and guiding and damping means (7) connecting said upper and lower connecting elements (5, 6), said guiding and damping means (7) and said upper and lower connecting elements (5, 6) being constructed with relation to each other so there is an axis of rotation C situated at the level of the upper vertebra and that there is a sliding of this axis due to the oblong groove (71) in order to limit the stresses on the anchoring screws (3) ensuring the connectors (2) are adapted to be fixed in said superjacent vertebra (Va),
wherein the prosthesis comprises limitation means (8) connecting the connectors (2, 4) between each other and allowing the flexion extension and lateral inflexion movements around the rotation and sliding axis C to be limited.

2. The total joint arthroplasty prosthesis according to claim 1, wherein the limitation means (8) are constituted of a cable (80) connecting the connectors (2, 4) between each other.

3. The total joint arthroplasty prosthesis according to claim 1, wherein the guiding and damping means (7) are constituted of a connection support (70) comprising an oblong groove (71) inside of which is housed a guiding element (72) cooperating with the connecting element (5, 6) and elastomer stops (73) whose elastic deformations allow the displacements of said guiding element (72) inside said oblong groove (71) to be limited without constraint and guiding and fixation means cooperating with the lower connecting element (6).

4. The total joint arthroplasty prosthesis according to claim 3, wherein the guiding element (72) is constituted of a first plate (74) integral with a hollow sleeve (75) on which a second plate (76) comes, said guiding element (72) being connected to the upper connecting element (5) through a clamping screw (77) traversing the hollow sleeve (75) to cooperate with a nut (78), said hollow sleeve (75) traversing the oblong groove (71) of the connection support (70) such that said hollow sleeve (75) displacements are limited by the elastic deformation of the elastomer stops (73).

5. The total joint arthroplasty prosthesis according to claim 3, wherein the connection support (70) is connected to the lower connecting element (6) by one of means of a guiding device (79, 63) and means of a blocking device (66, 65, 9).

6. The total joint arthroplasty prosthesis according to claim 1, wherein the upper connecting element (5) is comprised of a central body (51) extending at each end by rods (52) on which a slit bush with a spherical profile (53) respectively slides intended to cooperate with each first connector (2), said central body (51) being pierced by an oblong hole (54) for cooperation with the guiding and damping means (7).

7. The total joint arthroplasty prosthesis according to claim 5, wherein the lower connecting element (6) is constituted of a central part (60) laterally comprising extensions (61), each presenting a fork-shaped end (62) provided to come around the corresponding anchoring screw (3), said central part (60) comprising a guiding device (63) and threaded bores (65) for the placement and immobilization of the guiding and damping means (7).

8. The total joint arthroplasty prosthesis according to claim 1, wherein the first connectors (2) are each constituted of a body (20) presenting a bore (21) for the passage of the pedicle screw (3), a housing (22) for the reception of the first upper connection element (5), a threaded bore (24) perpendicularly culminating in a hole (25) and cooperating with a clamping screw (27) for immobilizing the limitation means (8) when the limitation means (8) are introduced in the hole (25), and a slot (26) traversing the hole (25) and the bore (21) to culminate inside the housing (22) so as to allow said housing to be deformed under a pressure force generated by a clamping nut (34) during immobilization of said first connector (2) on the corresponding pedicle screw (3).

9. The total joint arthroplasty prosthesis according to claim 1, wherein the second connectors (4) are each constituted of one of a connection element (40) forming a rod comprising, along a horizontal direction, a fork (41) presenting an oblong opening (43) for said fork's passage around the pedicle screw (3), and extending along a perpendicular direction by an anchoring rod (42) equipped with an end in the shape of a strip and a connecting ring (45) pierced in said connecting ring's middle by a hole (46) for said connecting ring placement around the same anchoring screw (3), said connecting ring (45) is pierced by through holes (49) allowing the limitation means (8) to be positioned and immobilized.

10. The total joint arthroplasty prosthesis according to claim 9, wherein the connecting ring (45) comprises lower lateral edges (47) cooperating with a fork (41) such that the connecting ring (45) cannot pivot in rotation with relation to the anchoring screw (3) when a nut (34) is tightened.

11. The total joint arthroplasty prosthesis according to claim 10, wherein the connecting ring (45) comprises upper lateral edges (48) that are disposed according to a direction perpendicular to that of lower lateral edges (47) for guiding the second lower connecting element (6).

12. A total joint arthroplasty prosthesis allowing the guiding elements of a superjacent Va and subjacent Vb lumbar vertebrae of a spinal segment Sr of a vertebral column to be reconstructed, the prosthesis comprising:
connectors (2, 4) adapted to be fixed in pedicles Vp of the spinal levels by anchoring screws (3), upper and lower connecting elements (5, 6) connecting the connectors (2, 4) between each other, and guiding and damping means (7) connecting said upper and lower connecting elements (5, 6), said guiding and damping means (7) and said upper and lower connecting elements (5, 6) being constructed with relation to each other so there is an axis of rotation C situated at the level of the upper vertebra and that there is a sliding of this axis due to the oblong groove (71) in order to limit the stresses on the anchoring screws (3) ensuring the connectors (2) are adapted to be fixed in said superjacent vertebra (Va),
wherein the upper connecting element (5) is comprised of a central body (51) extending at each end by rods (52) on which a slit bush with a spherical profile (53) respectively slides intended to cooperate with each first connector (2), said central body (51) being pierced by an oblong hole (54) for cooperation with the guiding and damping means (7).

* * * * *